US006953767B2

(12) United States Patent
Janssen et al.

(10) Patent No.: US 6,953,767 B2
(45) Date of Patent: Oct. 11, 2005

(54) SILICOALUMINOPHOSPHATE MOLECULAR SIEVE

(75) Inventors: Marcel J. G. Janssen, Kessel Lo (BE); An Verberckmoes, Serskamp (BE); Machteld M. Mertens, Boortmeerbeek (BE); Antonie Jan Bons, Kessel-Lo (BE); Wilfried J. Mortier, Kessel Lo (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 349 days.

(21) Appl. No.: 10/092,792

(22) Filed: Mar. 7, 2002

(65) Prior Publication Data

US 2002/0165090 A1 Nov. 7, 2002

Related U.S. Application Data

(63) Continuation-in-part of application No. 09/924,016, filed on Aug. 7, 2001, now Pat. No. 6,812,372.
(60) Provisional application No. 60/272,061, filed on Mar. 1, 2001.

(51) Int. Cl.[7] .................. C01B 33/26; B01J 27/182; C07C 1/20; C07C 1/207; C07C 1/247
(52) U.S. Cl. ................. 502/214; 423/327.1; 423/328.2; 423/329.1; 585/638; 585/639
(58) Field of Search ............. 423/328.1, 328.2, 423/329.1, 327.1; 502/214

(56) References Cited

U.S. PATENT DOCUMENTS

| | | | |
|---|---|---|---|
| 3,258,455 A | 6/1966 | Natta et al. ................. 260/93.7 |
| 3,305,538 A | 2/1967 | Natta et al. ................. 260/93.7 |
| 3,364,190 A | 1/1968 | Emrick ....................... 260/93.7 |
| 3,635,803 A | 1/1972 | Binns et al. .................. 204/80 |
| 3,645,992 A | 2/1972 | Elston ....................... 260/80.78 |
| 4,068,136 A | 1/1978 | Minami ....................... 307/353 |
| 4,076,698 A | 2/1978 | Anderson et al. ............ 526/348 |
| 4,243,691 A | 1/1981 | Mohlenkamp, Jr et al. . 426/649 |
| 4,302,565 A | 11/1981 | Goeke et al. .................. 526/88 |
| 4,440,871 A | 4/1984 | Lok et al. .................... 502/214 |
| 4,499,327 A | 2/1985 | Kaiser ........................ 585/640 |
| 4,659,685 A | 4/1987 | Coleman, III et al. ...... 502/113 |
| 5,191,141 A | 3/1993 | Barger et al. ............... 585/640 |
| 5,279,810 A | 1/1994 | Calabro ....................... 423/701 |
| 5,324,493 A * | 6/1994 | Mueller et al. ........... 423/328.2 |
| 5,324,800 A | 6/1994 | Welborn, Jr. et al. ....... 526/160 |
| 5,609,843 A | 3/1997 | Wendelbo ..................... 423/306 |
| 5,649,843 A | 7/1997 | Elger ............................. 440/38 |
| 5,892,079 A | 4/1999 | Wilson, Jr. ..................... 556/11 |
| 5,912,393 A | 6/1999 | Barger et al. ............... 585/640 |
| 6,207,872 B1 | 3/2001 | Barger et al. ............... 585/640 |
| 6,294,493 B1 * | 9/2001 | Strohmaier et al. ....... 423/328.2 |
| 6,334,994 B1 | 1/2002 | Wendelbo et al. ........... 423/718 |
| 6,514,899 B1 * | 2/2003 | Mertens et al. ........... 423/328.2 |

FOREIGN PATENT DOCUMENTS

| | | | |
|---|---|---|---|
| CN | 1088483 | 6/1994 | |
| WO | WO 93/13013 | 7/1993 | ........... C01B/25/45 |
| WO | WO 95/05342 | 2/1995 | ........... C01B/25/45 |
| WO | WO 98/15496 | 4/1998 | ........... C01B/25/45 |

OTHER PUBLICATIONS

Xu, Yan, et al, "The Synthesis of SAPO–34 and CoSAPO–34 from a Triethylamine–Hydrofluoric Acid–Water System," *J. Chem. Soc. Faraday Trans.*, vol. 86(2), 1990, pp. 425–429, no month.

(Continued)

Primary Examiner—Wayne A. Langel

(57) ABSTRACT

The present invention relates to a silicoaluminophosphate molecular sieve comprising at least one intergrown phase of molecular sieves having AEI and CHA framework types, wherein said intergrown phase has an AEI/CHA ratio of from about 5/95 to 40/60 as determined by DIFFaX analysis, using the powder X-ray diffraction pattern of a calcined sample of said silicoaluminophosphate molecular sieve. It also relates to methods for its preparation and to its use in the catalytic conversion of methanol to olefins.

16 Claims, 7 Drawing Sheets

OTHER PUBLICATIONS

Treacy, M.M.J., et al, "A General Recusion Method for Calculating Diffracted Intensities from Crystals Containing Planar Faults," Proceedings of the Royal Chemical Society, London, vol. 433, 1991, pp. 499–520, no month.

Treacy, M.M.J., et al, "Collection of Simulated XRD Powder Patterns for Zeolites", published on behalf of the Structure Commission of the International Zeolite Association, 2001, no month.

Simmen, A., et al, "The Structure Determination and Rietveld Refinement of the Aluminophosphate $AlPO_4\text{-}18$," Zeolites, vol. 11, Sep./Oct. 1991, pp. 654–661.

Chen, J., et al "SAPO–18 Catalysts and Their Bronsted Acid Sites," J. Phys. Chem., vol. 98, 1994, pp. 10216–10224, no month.

Chen, J., et al, "Silicoaluminophosphate Number Eighteen (SAPO–18): a New Microporous Solid Acid Catalyst," Catalysis Letters vol. 28, 1994, pp. 241–248, no month.

Lillerud, Karl Petter, et al, "Systematic Relationships Between the Structures of CHA, AEI and KFI," Zeolites and Related Microporous Materials: State of the Art 1994, Studies in Surface Science and Catalysis, vol. 84, 1994, pp. 543–550, no month.

Chen, J., et al, "Understanding the Bronsted Acidity of SAPO–5, SAPO–17, SAPO–18 and SAPO–34 and Their Catalytic Performance for Methanol Conversion to Hydrocarbons," Zeolites and Related Microporous Materials: State of the Art 1994, Studies in Surface Science and Catalysis, vol. 84, 1994, pp. 1731–1738, no month.

Prakash, A.M., et al, "Synthesis of SAPO–34: High Silicon Incorporation in the Presence of Morpholine as Template," J. Chem. Soc. Faraday Trans., 1994 90(15), pp. 2291–2296, no month.

Zenz, F.A., et al, Fluidization and Fluid–Particle Systems, Reinhold Publishing, New York, pp. 48–59, no date.

Kunii, D., et al, Fluidization Engineering, John Wiley & Sons, New Yorik, pp. 76–80, no date.

Inui, T., et al, "Preparation of Silico–Alumino–Phosphates by the Rapid Crystallization Method and Their Catalytic Performance in the Conversion of Methanol to Light Olefins", Applied Catalysis, 58 (1990), pp. 155–163, no month.

Abstract –Querini, C.A., et al, "Coke and Product Profiles Formed Along the Catalyst Bed During n–Heptane Reforming", Journal of Catalysis, vol. 141, Issue 2, Jun. 1993, pp. 389–406.

Abstract –Fung, S.C., et al, "A Highly Sensitive Detection Method for Temperature Programmed Oxidation of Coke Deposits: Methanation of $CO_2$", Journal of Catalysis, vol. 138, Issue 1, Nov. 1992, pp. 240–254.

* cited by examiner

SILICOALUMINOPHOSPHATE MOLECULAR SIEVE

This application claims priority to U.S. Provisional Patent Application No. 60/272,061, filed Mar. 1, 2001, and is a continuation-in-part of U.S. patent application Ser. No. 09/924,016, filed Aug. 7, 2001, now U.S. Pat. No. 6,812,372 which is fully incorporated herein by reference.

FIELD OF THE INVENTION

This invention relates to new silicoaluminophosphate molecular sieves, to methods of making them and to their use in a method of making an olefin product by contacting these silicoaluminophosphate molecular sieves with an oxygenate feedstock. In particular, this invention relates to silicoaluminophosphate molecular sieves comprising at least one intergrown phase of AEI and CHA molecular sieves.

BACKGROUND OF THE INVENTION

Silicoaluminophosphate (SAPO) molecular sieves contain a three-dimensional microporous crystal framework structure of $[SiO_2]$, $[AlO_2]$ and $[PO_2]$ corner sharing tetrahedral units. The $[PO_2]$ tetrahedral units are provided by a variety of compositions including phosphoric acid, organic phosphates such as triethyl phosphate, and aluminophosphates. The $[AlO_2]$ tetrahedral units are provided by a variety of compositions including aluminum alkoxides such as aluminum isopropoxide, aluminum phosphates, aluminum hydroxide, sodium aluminate, and pseudoboehmite. The $[SiO_2]$ tetrahedral units are provided by a variety of compositions including silica sols and silicon alkoxides such as tetraethylorthosilicate and fumed silica.

Aluminophosphate (ALPO) molecular sieves are crystalline microporous oxides which can have an $AlPO_4$ framework. ALPOs can have additional elements within the framework, typically have uniform pore dimensions ranging from about 3 Angstroms to about 10 Angstroms.

Light olefins, particularly ethylene and propylene, can be produced by contacting a feedstock containing oxygenated organic compounds, such as methanol or dimethyl ether, with a SAPO and/or ALPO-containing catalyst. See for example U.S. Pat. No. 4,499,327.

SAPO-34 and SAPO-18 have been reported as suitable catalysts for light olefin production from methanol. SAPO-34 belongs to the family of molecular sieves having the structure type of the zeolitic mineral chabazite (CHA). The preparation and characterization of SAPO-34 has been reported in several publications, including U.S. Pat. No. 4,440,871; J. Chen et al. in "Studies in Surface Science and Catalysis", Vol. 84, pp. 1731–1738; U.S. Pat. No. 5,279,810; J. Chen et al. in "Journal of Physical Chemistry", Vol. 98, pp. 10216–10224 (1994); J. Chen et al. in "Catalysis Letters", Vol. 28, pp. 241–248 (1994); A. M. Prakash et al. in "Journal of the Chemical Society, Faraday Transactions" Vol. 90(15), pp. 2291–2296 (1994); Yan Xu et al. in "Journal of the Chemical Society, Chemical Society, Faraday Transactions" Vol. 86(2), pp. 425–429 (1990), all of which are herein fully incorporated by reference.

SAPO-18 belongs to the family of molecular sieves having the AEI structure type. Other molecular sieves with the AEI structure type are ALPO-18 and RUW-18. The preparation and characterization of molecular sieves with AEI structure type has been reported in several publications, including U.S. Pat. No. 4,440,871; J. Chen et al. in "Studies in Surface Science and Catalysis", Vol. 84, pp. 1731–1738; U.S. Pat. No. 5,279,810; J. Chen et al. in "Journal of Physical Chemistry", Vol. 98, pp. 10216–10224 (1994); J. Chen et al. in "Catalysis Letters", Vol. 28, pp. 241–248 (1994); A. M. Prakash et al. in "Journal of the Chemical Society, Faraday Transaction" Vol. 90 (15), pp. 2291–2296 (1994); Yan Xu et al. in "Journal of the Chemical Society, Faraday Transactions" Vol. 86(2), pp. 425–429 (1990); U.S. Pat. No. 5,609,843, all of which are herein fully incorporated by reference.

International Application PCT/NO97/00272, published as WO 98/15496, relates to a molecular sieve that is a mixed phase comprising silicoaluminophosphates of AEI and CHA structure, referred to as RUW-19. RUW-19 is said to produce an X-ray diffractogram that includes peaks at the following 2θ values: 9.3–9.5, 10.4–10.6, 12.7–12.9, 13.8–14.0, 15.9–16.1, 16.7–16.9, 18.9–19.0, 20.5–10.7, 21.0–21.3, 23.7–24.0, 25.7–26.0, 30.9–31.1. FIG. 1 of this publication shows the XRD-traces in the 15–33 (2θ) region for RUW-19 (examples 1 to 3), SAPO-18 (example 4), SAPO-34 (example 5) and a physical mixture of SAPO-18 and SAPO-34 (example 6). This publication suggests that RUW-19 is different from a physical mixture of SAPO-18 and SAPO-34. RUW-19 has peaks characteristic of an AEI structure type molecular sieve, except that the broad feature centered at about 16.9 (2θ) in RUW-19 replaces the pair of reflections centered at about 17.0 (2θ) in SAPO-18 or AEI. Also, RUW-19 does not have the reflections associated with SAPO-34 or CHA centered at 17.8 (2θ) and 24.8 (2θ). According to WO 98/15496, RUW-19 is suitable for the conversion of methanol to olefins. Throughout this description, the XRD reflection values are referred to as (2θ), which is synonymous to the expression "degrees 2θ".

In the conversion of methanol to olefins, SAPO-34 exhibits relatively high product selectivity to ethylene and propylene, and low product selectivity to paraffin and olefin with four or more carbons ($C_4^+$ olefin). Catalysts containing SAPO-34 are thus particularly suited for the conversion of methanol to olefin. Despite its good performances, carbonaceous deposits, commonly referred to as coke, quickly form in the catalytic cages of SAPO-34. Eventually, the presence of too much coke will clog up the cage and deactivate the catalyst. Also, despite its low product selectivity to paraffin, SAPO-34 still produces by-products. Separating by-products from the desired ethylene and propylene adds additional cost to the methanol to olefin conversion process. Therefore, there is a need to find new molecular sieves that have good product selectivity and produce few by-products.

SUMMARY OF THE INVENTION

The present invention relates to silicoaluminophosphate molecular sieves comprising at least one intergrown phase of molecular sieves having AEI and CHA framework types, wherein said intergrown phase has an AEI/CHA ratio of from about 5/95 to 40/60 as determined by DIFFaX analysis, using the powder X-ray diffraction pattern of a calcined sample of said silicoaluminophosphate molecular sieve.

The silicoaluminophosphate molecular sieves of the present invention exhibit characteristic X-ray diffraction features. In an embodiment of the invention, the molecular sieves of the invention possess silica to alumina molar ratios ($SiO_2/Al_2O_3$) ranging from 0.01 to 0.25.

The molecular sieves of the present invention may conveniently be prepared by a process that comprises a) combining a reactive source of silicon, a reactive source of phosphorus and a hydrated aluminum oxide in the presence of an organic structure directing agent (template) to form a mixture; b) mixing and heating continuously the mixture prepared at step a) up to the crystallization temperature; c) maintaining the mixture at the crystallization temperature and under stirring for a period of time of from 2 to 150 hours; d) recovering crystals of the silicoaluminophosphate molecular sieve wherein the mixture prepared at step a) has a molar composition within the following ranges:

$P_2O_5:Al_2O_3$ from 0.6:1 to 1.2:1

$SiO_2:Al_2O_3$ from 0.005:1 to 0.35:1

$H_2O:Al_2O_3$ from 10:1 to 40:1 and the template is a tetraethylammonium compound. In an embodiment of the invention, the organic structure directing agent is tetraethylammonium hydroxide.

The silicoaluminophosphate molecular sieves of the present invention exhibit good catalytic performances in processes for making olefin products from an oxygenate feedstock, such as a feedstock comprising methanol.

DETAILED DESCRIPTION OF THE INVENTION

Figure 1A:
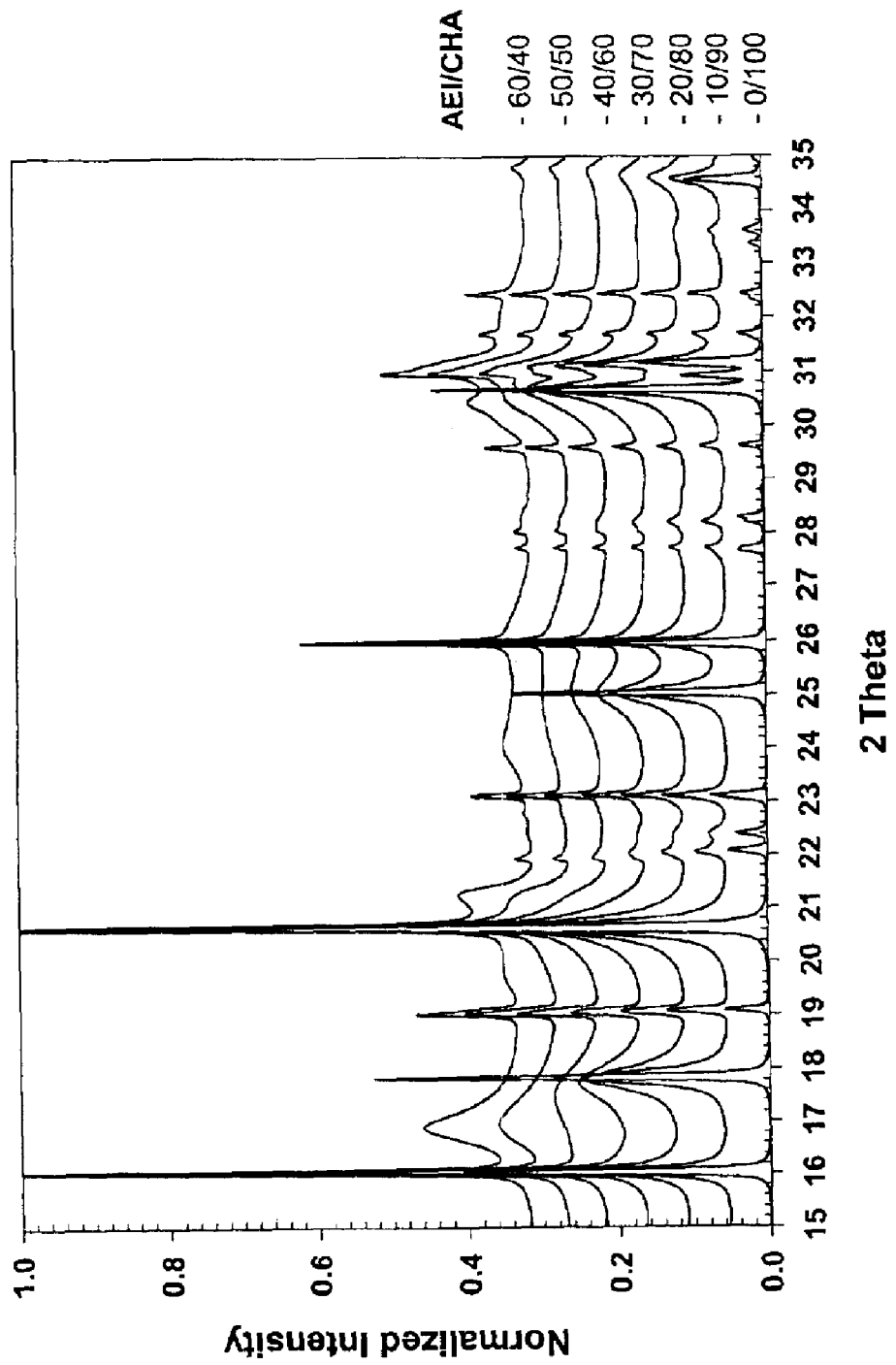
FIGS. 1a and 1b show DIFFaX simulated diffraction patterns for intergrown phases having various AEI/CHA ratios.

The present invention relates to a silicoaluminophosphate molecular sieve comprising at least one intergrown phase of molecular sieves having AEI and CHA framework types, wherein said intergrown phase has an AEI/CHA ratio of from about 5/95 to 40/60 as determined by DIFFaX analysis, using the powder X-ray diffraction pattern of a calcined sample of said silicoaluminophosphate molecular sieve.

Intergrown molecular sieve phases are disordered planar intergrowths of molecular sieve frameworks. We refer to the "Catalog of Disordered Zeolite Structures", 2000 Edition, published by the Structure Commission of the International Zeolite Association and to the "Collection of Simulated XRD Powder Patterns for Zeolites", M. M. J. Treacy and J. B. Higgins, 2001 Edition, published on behalf of the Structure Commission of the International Zeolite Association for a detailed explanation on intergrown molecular sieve phases.

Regular crystalline solids are periodically ordered in three dimensions. Structurally disordered structures show periodic ordering in dimensions less than three, i.e. in two, one or zero dimensions. This phenomenon is called stacking disorder of structurally invariant Periodic Building Units. Crystal structures built from Periodic Building Units are called end-member structures if periodic ordering is achieved in all three dimensions. Disordered structures are those where the stacking sequence of the Periodic Building Units deviates from periodic ordering up to statistic stacking sequences.

The molecular sieves of the present invention are disordered planar intergrowths of end-member structures AEI and CHA. We refer to A. Simmen et al. in Zeolites (1991), Vol. 11, pp. 654–661 describing the structure of molecular sieves with AEI and CHA framework types. For AEI and CHA, the Periodic Building Unit is a double six ring layer. There are two types of layers "a" and "b", which are identical except "b" is the mirror image of "a" (180° rotation about the plane normal or mirror operation perpendicular to the plane normal). When layers of the same type stack on top of one another, i.e. aaa or bbb, the framework type CHA is generated. When layers "a" and "b" alternate, ie, abab, the framework type AEI is generated. The molecular sieves of the present invention are made of stackings of layers "a" and "b" which contain regions of CHA framework type and regions of AEI framework type. Each change of CHA to AEI framework type is a stacking disorder or planar fault.

Preferably, the molecular sieves of the invention possess an AEI/CHA ratio of from about 7/93 to 38/62, more preferably from about 8/92 to 35/65, even more preferably from about 9/91 to 33/67, most preferably from about 10/90 to 30/70 as determined by DIFFaX analysis, using the powder X-ray diffraction pattern of a calcined sample of said silicoaluminophosphate molecular sieve.

In the case of crystals with planar faults, interpretation of XRD diffraction diffraction patterns requires an ability to simulate the effects of stacking disorder. DIFFaX is a computer program based on a mathematical model for calculating intensities from crystals containing planar faults (see M. M. J. Tracey et al., Proceedings of the Royal Chemical Society, London, A (1991), Vol. 433, pp. 499–520). DIFFaX is the simulation program selected by and available from the International Zeolite Association to simulate the XRD powder patterns for intergrown phases of zeolites (see "Collection of Simulated XRD Powder Patterns for Zeolites" by M. M. J. Treacy and J. B. Higgins, 2001, Fourth Edition, published on behalf of the Structure Commission of the International Zeolite Association). It has also been used to theoretically study intergrown phases of AEI, CHA, tmm and KFI, as reported by K. P. Lillerud et al. in "Studies in Surface Science and Catalysis", 1994, Vol. 84, pp. 543–550. DIFFaX is a well-known and established method to characterize crystalline materials with planar faults such as the intergrown molecular sieves of the present invention.

Figure 1B:
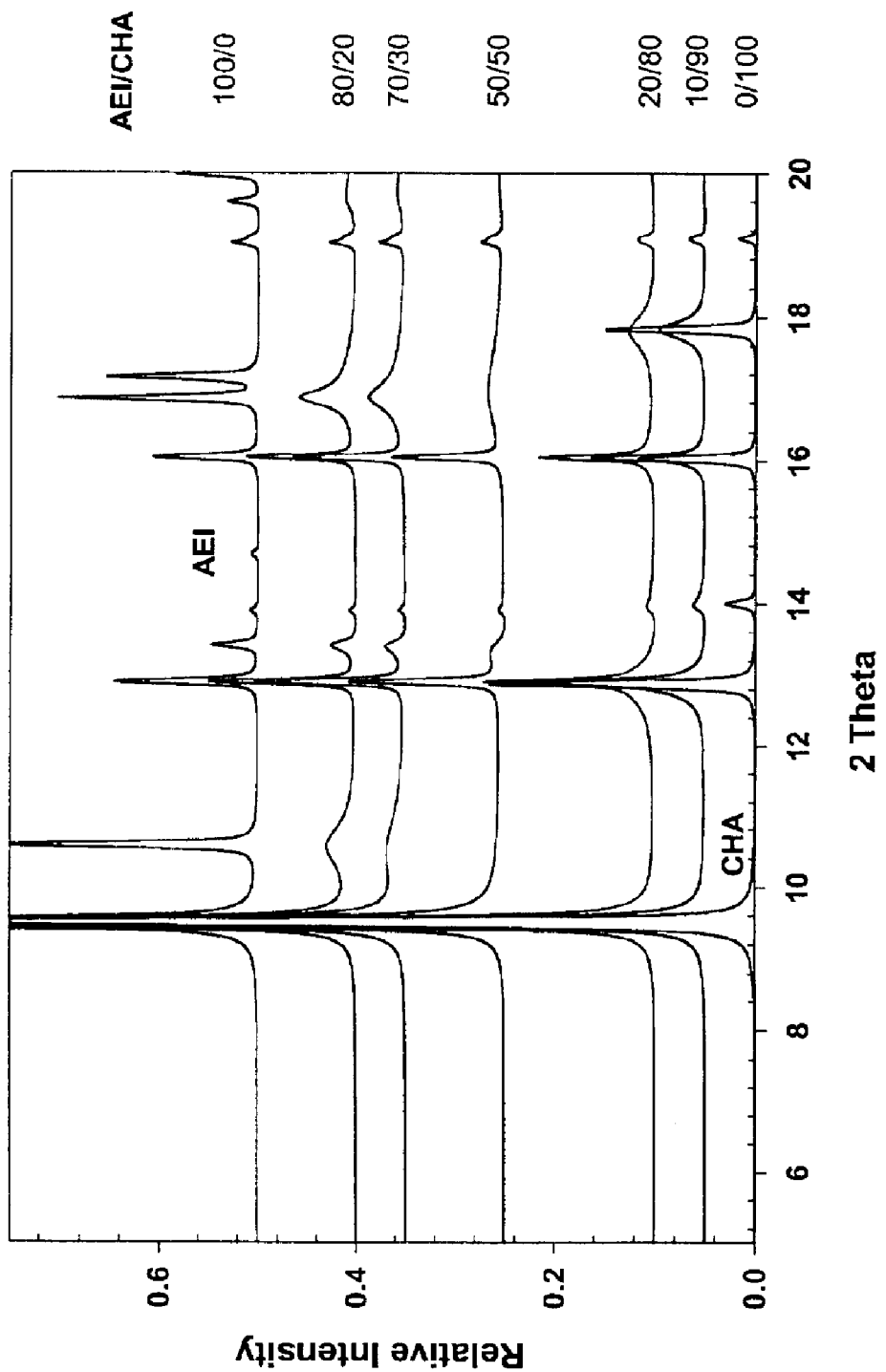

FIGS. 1a and 1b show the simulated diffraction patterns obtained for intergrown phases having various AEI/CHA ratios. FIG. 1a shows the diffraction patterns in the 15 to 35 (2θ) range simulated by DIFFaX for intergrown phases with AEI/CHA ratios of 0/100 (CHA end-member), 10/90 (AEI/CHA=0.11), 20/80 (AEI/CHA=0.25), 30/70 (AEI/CHA=0.41), 40/60 (AEI/CHA=0.67), 50/50 (AEI/CHA=1.00) and 60/40 (AEI/CHA=1.50). FIG. 1b shows the diffraction patterns in the range of 5 to 20 (2θ) simulated by DIFFaX for intergrown phases with AEI/CHA ratios of 0/100 (CHA end-member), 10/90 (AEI/CHA=0.11), 20/80 (AEI/CHA= 0.25), 50/50 (AEI/CHA=1.0), 70/30 (AEI/CHA=2.33), 80/20 (AEI/CHA=4.0), 100/0 (AEI end-member). All XRD diffraction patterns are normalized between 0 and 1. Normalized intensity values are determined by normalizing the intensities of the diffraction peaks to the intensity value of the reflection in the 20.5–20.7 (2θ) range. For example, if the peak in the 20.5–20.7 (2θ) range has an absolute intensity of 50 counts and the peak at 26.0 (2θ) has an absolute intensity of 16 counts, then the normalized intensity of the peak at 26.0 (2θ) is 0.32. Normalization of intensity values allows for the comparison between diffraction patterns of the intensity of an X-ray diffraction peak at certain 2θ value.

As the ratio of AEI increases relative to CHA in the intergrown phase, one can observe a decrease in intensity of certain peaks, for example, the peak at about 2θ=25.0 and an increase in intensity of other peaks, for example the peak at about 2θ=17.05 and the shoulder at 2θ=21.2. Intergrown phases with AEI/CHA ratios of 50/50 and above (AEI/CHA≧1.0) show a broad feature centered at about 16.9 (2θ).

Figure 2:
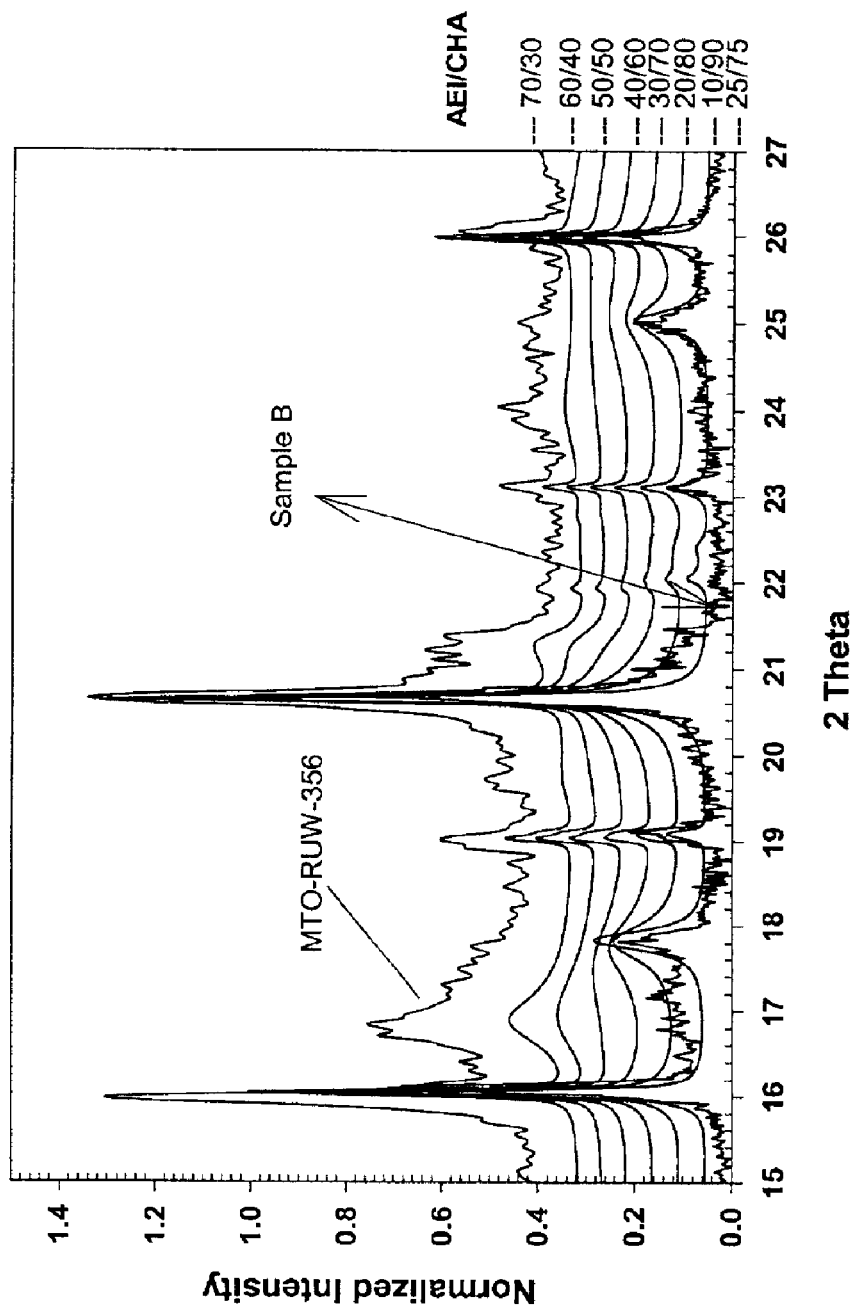
FIG. 2 shows the XRD diffraction pattern of a silicoaluminophosphate according to the invention, of MTO-RUW-356 of WO 98/15496 and DIFFaX simulated diffraction patterns for intergrown phases having various AEI/CHA ratios.

FIG. 2 shows the powder XRD diffraction pattern of a silicoaluminophosphate according to the present invention (Sample B) and, by way of comparison, the XRD diffraction pattern of MTO-RUW-356 described in example 1 and FIG. 1 of WO 98/15496 as well as DIFFaX simulated diffraction patterns for intergrowths with varying AEI/CHA ratios. The diffraction pattern of MTO-RUW-356 was digitized and re-normalized. DIFFaX analysis indicates that Sample B according to the present invention has an AEI/CHA ratio of 25/75 (AEI/CHA ratio of 0.33) and that MTO-RUW-356 has an AEI/CHA ratio of 70/30 (AEI/CHA ratio of 2.3). MTO-RUW-356 has a broad feature centered at about 16.9 (2θ).

The silicoaluminophosphates of the present invention are characterized by powder XRD diffraction patterns obtained from samples after calcination and avoiding re-hydration after calcination, having at least the reflections in the 5 to 25 (2θ) range as shown in Table 1:

TABLE 1

| 2θ (CuKα) |
| --- |
| 9.3–9.6 |
| 12.7–13.0 |
| 13.8–14.0 |
| 15.9–16.1 |
| 17.7–18.1 |
| 18.9–19.1 |
| 20.5–20.7 |
| 23.7–24.0 |

The XRD diffraction patterns of the intergrown phases of AEI/CHA according to the present invention are also characterized by the absence of peaks in the 9.8 to 12.0 (2θ) range and the absence of any broad feature centered at about 16.9 (2θ). A further characteristic is the presence of a peak in the 17.7 to 18.1 (2θ) range. The reflection peak in the 17.7–18.1 (2θ) range has a relative intensity between 0.09 and 0.4, preferably between 0.1 and 0.35 with respect to the reflection peak at 17.9 (2θ) in the diffraction pattern of SAPO-34, all diffraction patterns being normalized to the intensity value of the reflection peak in the 20.5–20.7 (2θ) range.

Figure 3:
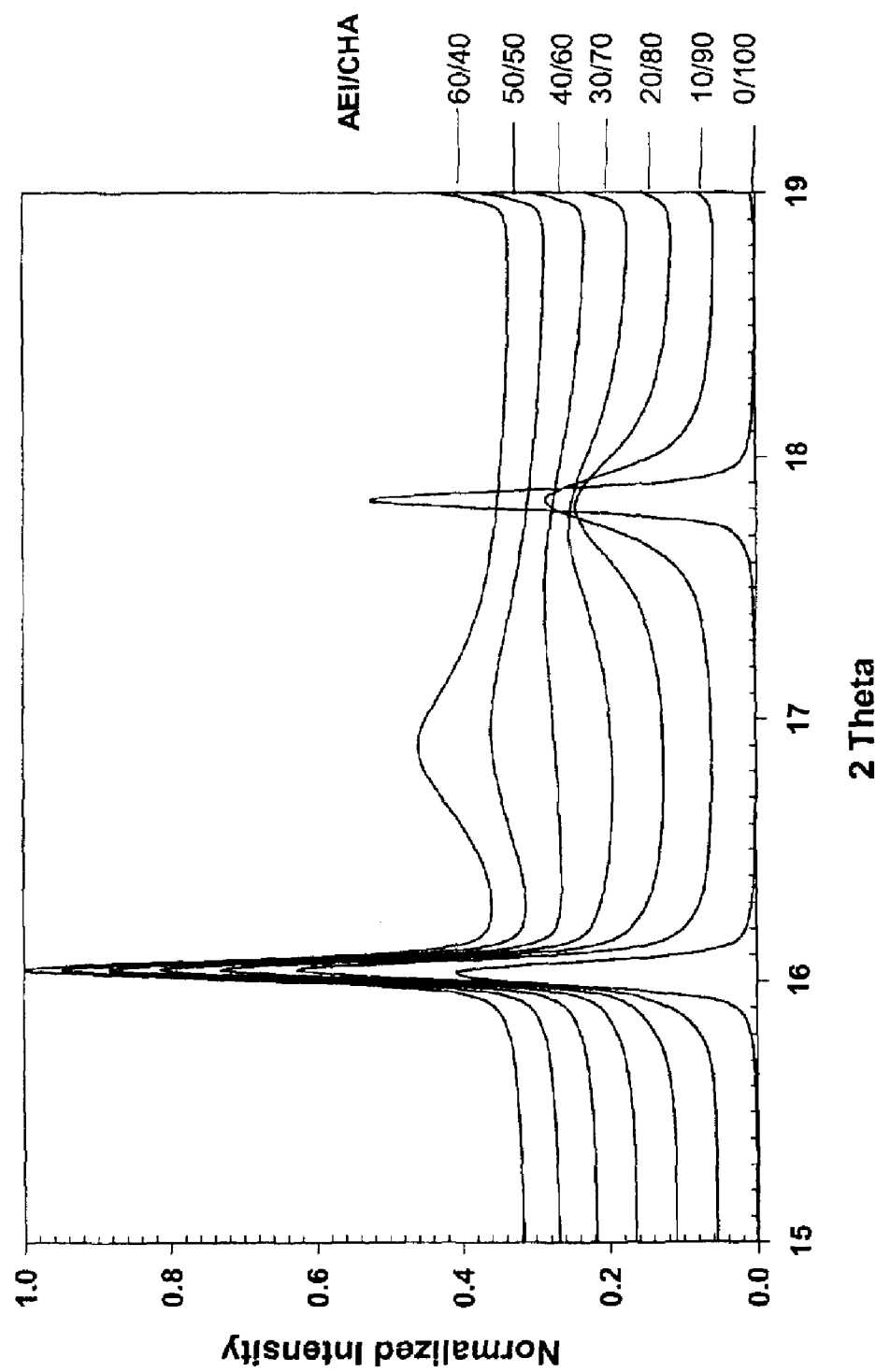
FIG. 3 shows DIFFaX simulated diffraction patterns in the 15 to 19 2θ range for intergrown phases having various AEI/CHA ratios.

FIG. 3 illustrates the evolution of these XRD features in the 15 to 19 (2θ) range for AEI/CHA ratios of 0/100 (CHA end-member), 10/90 (AEI/CHA=0.11), 20/80 (AEI/CHA=0.25), 30/70 (AEI/CHA=0.41), 40/60 (AEI/CHA=0.67), 50/50 (AEI/CHA=1.00) and 60/40 (AEI/CHA=1.50).

The silicoaluminophosphate molecular sieves of the present invention comprise at least one intergrown phase of AEI and CHA molecular sieves. Preferably the CHA molecular sieve is SAPO-34 and the AEI molecular sieve is selected from SAPO-18, ALPO-18 or a mixture of SAPO-18 and ALPO-18. Preferably, the silicoaluminophosphates of the present invention have a silica to alumina molar ratios ($SiO_2/Al_2O_3$) ranging from 0.01 to 0.25, more preferably from 0.02 to 0.20, even more preferably from 0.03 to 0.19, most preferably from 0.03 to 0.08. The silica to alumina molar ratio ($SiO_2/Al_2O_3$) is conveniently determined by chemical analysis.

In one embodiment, the silicoaluminophosphates of the present invention are prepared by submitting a mixture comprising a reactive source of silicon, a reactive source of aluminum and a reactive source of phosphorus, in the presence of an organic structure directing agent (template) to hydrothermal treatment under autogenous pressure.

The molecular sieves of the present invention may conveniently be prepared by a process that comprises a) combining a reactive source of silicon, a reactive source of phosphorus and a hydrated aluminum oxide in the presence of an organic structure directing agent (template) to form a mixture;

b) mixing and heating continuously the mixture prepared at step a) up to the crystallization temperature;

c) maintaining the mixture at the crystallization temperature and under stirring for a period of time of from 2 to 150 hours;

d) recovering crystals of the silicoaluminophosphate molecular sieve wherein the mixture prepared at step a) has a molar composition within the following ranges:

$P_2O_5:Al_2O_3$ from 0.6:1 to 1.2:1

$SiO_2:Al_2O_3$ from 0.005:1 to 0.35:1

$H_2O:Al_2O_3$ from 10:1 to 40:1 and the template is a tetraethylammonium compound.

Preferably, the mixture prepared at step a) has a molar composition within the following ranges:

$P_2O_5:Al_2O_3$ from 0.8:1 to 1.1:1

$SiO_2:Al_2O_3$ from 0.01:1 to 0.3:1, most preferably from 0.015:1 to 0.25:1

$H_2O:Al_2O_3$ from 10:1 to 40:1.

It will be understood that the molar ratio of silica to alumina in the reaction mixture will influence the silica to alumina ratio of the molecular sieve after synthesis.

The reactive source of silicon used in the preparation of the silicoaluminophosphates of the invention may be a silicate, e.g., fumed silica, such as Aerosil (available form Degussa), a tetraalkyl orthosilicate, or an aqueous colloidal suspension of silica, for example one sold by E. I. du Pont de Nemours under the tradename Ludox.

Examples of suitable hydrated aluminum oxides that may be used according to the present invention include boehmite and pseudoboehmite. Preferably, pseudoboehmite is used.

The organic structure directing agent, also called template, is a tetraethyl ammonium compound selected from the group of tetraethyl ammonium hydroxide (TEAOH), tetraethyl ammonium phosphate, tetraethyl ammonium fluoride, tetraethyl ammonium bromide, tetraethyl ammonium chloride, tetraethyl ammonium acetate. Most preferably, the template is tetraethyl ammonium hydroxide.

In order to prepare the silicoaluminophosphates of the invention, the reaction mixture obtained by mixing the reactive sources of alumina, silica, phosphorus and organic structure directing agent is submitted to hydrothermal treatment. The reaction mixture is heated continuously up to the crystallization temperature that may range from about 120° C. and 250° C., preferably from 130° C. and 200° C., most preferably from 150° C. to 185° C. Heating up to the crystallization temperature is typically carried for a period of time ranging from about 5 to about 16 hours, preferably from about 6 to 12 hours, most preferably from about 6 to 9 hours.

The temperature may be increased stepwise or continuously. However, continuous heating is preferred. The reaction may be kept static, tumbled or stirred during heat-up. Preferably, the reaction is tumbled or stirred, most preferably stirred.

The temperature is then maintained at the crystallization temperature for a period of time ranging from 2 to 150 hours, the crystallization time depending mainly on the crystallization temperature. Heat is applied for a period of time effective to form crystalline product. In a specific embodiment, the reaction is kept at the crystallization temperature for a period of from 20 to 60 hours.

The silicoaluminophosphate synthesis may be aided by seeds form a previous synthesis or by seeds of another molecular sieve, conveniently, SAPO-34 seeds. Hydrothermal treatment may be carried out with or without agitation, for example stirring or tumbling (rotating the vessel about a horizontal axis), but is preferably carried out with agitation. Preferably, the mixture is stirred during the period required to heat the reaction mixture to the crystallization temperature and for the period of crystallization.

Typically, the crystalline molecular sieve product is formed as a slurry and can be recovered by standard means, such as by centrifugation or filtration. The separated molecular sieve product can also be washed, recovered by centrifugation or filtration and dried.

As a result of the molecular sieve crystallization process, the recovered molecular sieve contains within its pores at least a portion of the template used. The crystalline structure essentially wraps around the template, and the template should be removed to obtain catalytic activity. In a preferred embodiment, activation is performed in such a manner that the template is removed from the molecular sieve, leaving active catalytic sites with the microporous channels of the molecular sieve open for contact with a feedstock. The activation process is typically accomplished by calcining, or essentially heating the molecular sieve comprising the template at a temperature of from 200 to 800° C. in the presence of an oxygen-containing gas. In some cases, it may be desirable to heat the molecular sieve in an environment having a low oxygen concentration. This type of process can be used for partial or complete removal of the template from the intracrystalline pore system. In other cases, particularly with smaller templates, complete or partial removal from the sieve can be accomplished by conventional desorption processes.

Figure 4A:
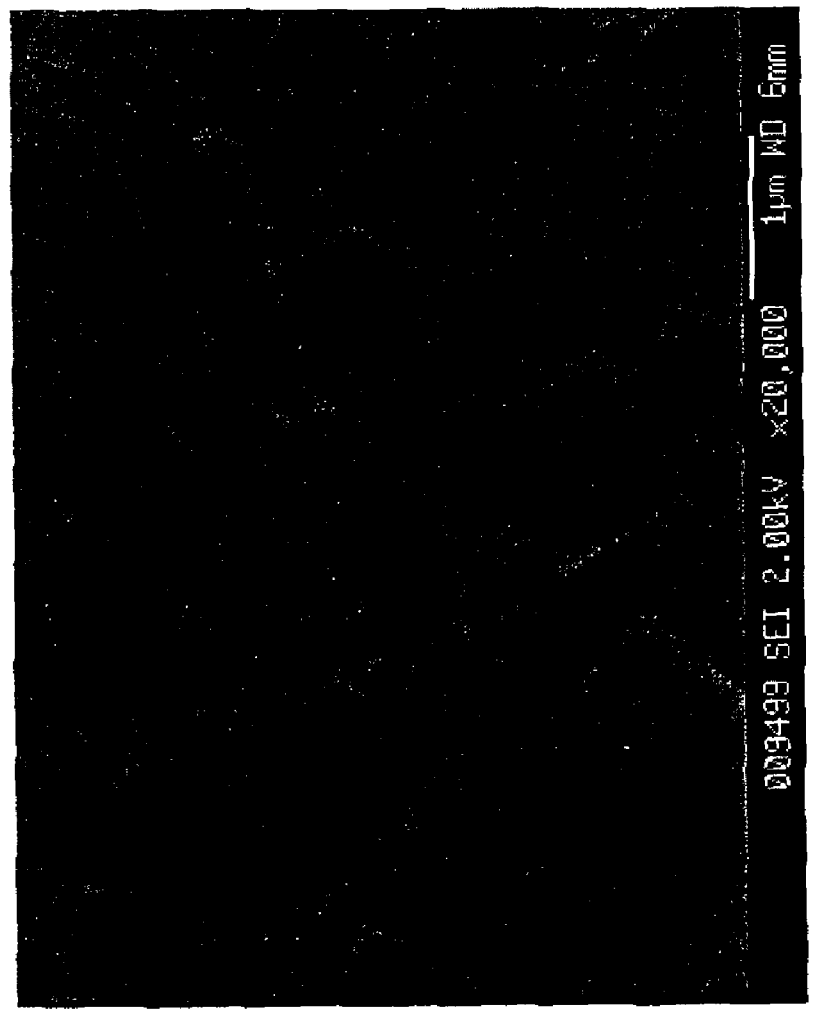
FIG. 4a shows a SEM picture of a crystalline silicoaluminophosphate molecular sieve according to the invention, obtained on a JEOL JSM-6340F Field Emission Scanning Electron Microscope, using a magnification of 20,000 times at a voltage of 2 keV.
Figure 4B:
FIG. 4b shows a TEM picture of a crystalline silicoaluminophosphate molecular sieve according to the invention.

The crystalline silicoaluminophosphate molecular sieves of the present invention are typically plates, platelets or stacked platelets. These plates, platelets of stacked platelets can be seen as flattened cubes with the smallest dimension being defined as Z and the largest dimension being defined as Y, preferably with Z/Y less than 1. Preferably, Z/Y is between 0.05 and 0.5. FIG. 4 shows an electron microscopy picture of a crystalline silicoaluminophosphate molecular sieve according to the invention. Preferably, the average smallest crystal dimension of the molecular sieve of the invention is less than 0.1 micron.

Once the molecular sieve is made, it can be formulated into a catalyst by combining the molecular sieve with other materials that provide additional hardness or catalytic activity to the finished catalyst product. When combined with these other materials, the resulting composition is typically referred to as a silicoaluminophosphate catalyst, with the catalyst comprising the SAPO molecular sieve. This invention also relates to catalysts comprising the molecular sieves of this invention.

Materials which can be blended with the molecular sieve can be various inert or catalytically active materials, or various binder materials. These materials include compositions such as kaolin and other clays, various forms of rare earth metals, other non-zeolite catalyst components, zeolite catalyst components, alumina or alumina sol, titania, zirconia, quartz, silica or silica sol, and mixtures thereof. These components are also effective in reducing overall catalyst cost, acting as a thermal sink to assist in heat shielding the catalyst during regeneration, densifying the catalyst and increasing catalyst strength. When blended with non-silicoaluminophosphate molecular sieve materials, the amount of molecular sieve which is contained in the final catalyst product ranges from 10 to 90 weight percent of the total catalyst, preferably 20 to 70 weight percent of the total catalyst.

The molecular sieves synthesized in accordance with the present method can be used to dry gases and liquids; for selective molecular separation based on size and polar properties; as ion-exchangers; as catalysts in cracking, hydrocracking, disproportionation, alkylation, isomerization, oxidation; as chemical carriers; in gas chromatography; and in the petroleum industry to remove normal paraffins from distillates.

The silicoaluminophosphates of the present invention are particularly suited for the catalytic conversion of oxygenates to hydrocarbons. Accordingly, the present invention also relates to a method for making an olefin product from an oxygenate feedstock wherein said oxygenate feedstock is contacted with the catalyst of this invention comprising the molecular sieve of this invention under conditions effective to convert the oxygenate feedstock to olefin products. When compared to other silicoaluminophosphates under the same operating conditions, the silicoaluminophosphates of the present invention exhibit higher selectivity to light olefins, and produce fewer by-products.

In this process a feedstock containing an oxygenate contacts a catalyst comprising the molecular sieve in a reaction zone of a reactor at conditions effective to produce light olefins, particularly ethylene and propylene. Typically, the oxygenate feedstock is contacted with the catalyst containing the molecular sieve when the oxygenate is in vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions.

In this oxygenate conversion process, olefins can generally be produced at a wide range of temperatures. An effective operating temperature range can be from about 200° C. to 700° C. At the lower end of the temperature range, the formation of the desired olefin products may become markedly slow. At the upper end of the temperature range, the process may not form an optimum amount of product. An operating temperature of at least 300° C., and up to 525° C. is preferred.

In a preferred embodiment, it is highly desirable to operate at a temperature of at least 300° C. and a Temperature Corrected Normalized Methane Sensitivity (TCNMS) of less than about 0.016, preferably less than about 0.012, more preferably less than about 0.01. It is particularly preferred that the reaction conditions for making olefin from oxygenate comprise a WHSV of at least about 20 $hr^{-1}$ producing olefins and a TCNMS of less than about 0.016.

As used herein, TCNMS is defined as the Normalized Methane Selectivity (NMS) when the temperature is less than 400° C. The NMS is defined as the methane product yield divided by the ethylene product yield wherein each yield is measured on, or is converted to, a weight % basis. When the temperature is 400° C. or greater, the TCNMS is defined by the following equation, in which T is the average temperature within the reactor in ° C.:

$$TCNMS = \frac{NMS}{1 + (((T - 400)/400) \times 14.84)}$$

The pressure also may vary over a wide range, including autogenous pressures. Preferred pressures are in the range of about 5 kPa to about 5 MPa, with the most preferred range being of from about 50 kPa to about 0.5 MPa. The foregoing pressures are exclusive of any oxygen depleted diluent, and thus, refer to the partial pressure of the oxygenate compounds and/or mixtures thereof with feedstock.

The process can be carried out in a dynamic bed system or any system using a variety of transport beds, although a fixed bed system could be used. It is particularly desirable to operate the reaction process at high space velocities.

The process may be carried out in a batch, semi-continuous or continuous fashion. The process can be conducted in a single reaction zone or a number of reaction zones arranged in series or in parallel.

The conversion of oxygenates to produce olefins is preferably carried out in a large scale continuous catalytic reactor. This type of reactor includes fluid bed reactors and concurrent riser reactors as described in "Free Fall Reactor," *Fluidization Engineering*, D. Kunii and O. Levenspiel, Robert E. Krieger Publishing Co. NY, 1977, incorporated in its entirety herein by reference. Additionally, countercurrent free fall reactors may be used in the conversion process. See, for example, U.S. Pat. No. 4,068,136 and "Riser Reactor", *Fluidization and Fluid-Particle Systems*, pages 48–59, F. A. Zenz and D. F. Othmo, Reinhold Publishing Corp., NY 1960, the descriptions of which are expressly incorporated herein by reference.

Any standard commercial scale reactor system can be used, for example fixed bed or moving bed systems. The commercial scale reactor systems can be operated at a weight hourly space velocity (WHSV) of from 1 hr$^{-1}$ to 1000 hr$^{-1}$. In the case of commercial scale reactors, WHSV is defined as the weight of hydrocarbon in the feedstock per hour per weight of silicoaluminophosphate molecular sieve content of the catalyst. The hydrocarbon content is the oxygenate content and the content of any hydrocarbon which may be present with the oxygenate. The silicoaluminophosphate molecular sieve content means only the silicoaluminophosphate molecular sieve portion that is contained within the catalyst. This excludes components such as binders, diluents, inerts, rare earth components, etc.

One or more inert diluents may be present in the feedstock, for example, in an amount of from 1 to 95 molar percent, based on the total number of moles of all feed and diluent components fed to the reaction zone. Typical diluents include, but are not necessarily limited to helium, argon, nitrogen, carbon monoxide, carbon dioxide, hydrogen, water, paraffins, alkanes (especially methane, ethane, and propane), alkylenes, aromatic compounds, and mixtures thereof. The preferred diluents are water and nitrogen. Water can be injected in either liquid or vapor form.

The level of conversion of the oxygenates is maintained to reduce the level of unwanted by-products. Conversion is also maintained sufficiently high to avoid the need for commercially undesirable levels of recycling of unreacted feeds. A reduction in unwanted by-products is seen when conversion moves from 100 mol % to about 98 mol % or less. Recycling up to as much as about 50 mol % of the feed is preferred. Therefore, conversions levels which achieve both goals are from about 50 mol % to about 98 mol % and, desirably, from about 85 mol % to about 98 mol %. However, it is also acceptable to achieve conversion between 98 mol % and 100 mol % in order to simplify the recycling process. Oxygenate conversion is maintained using a number of methods familiar to persons of ordinary skill in the art. Examples include, but are not necessarily limited to, adjusting one or more of the following: the reaction temperature; pressure; flow rate (i.e., WHSV); level and degree of catalyst regeneration; amount of catalyst re-circulation; the specific reactor configuration; the feed composition; and other parameters which affect the conversion.

If regeneration is used, the molecular sieve catalyst can be continuously introduced as a moving bed to a regeneration zone where it is be regenerated, such as for example by removing carbonaceous materials or by oxidation in an oxygen-containing atmosphere. In a preferred embodiment, the catalyst is subject to a regeneration step by burning off carbonaceous deposits accumulated during the conversion reactions.

The oxygenate feedstock comprises at least one organic compound which contains at least one oxygen atom, such as aliphatic alcohols, ethers, carbonyl compounds (aldehydes, ketones, carboxylic acids, carbonates, esters and the like). When the oxygenate is an alcohol, the alcohol can include an aliphatic moiety having from 1 to 10 carbon atoms, more preferably from 1 to 4 carbon atoms. Representative alcohols include but are not necessarily limited to lower straight and branched chain aliphatic alcohols and their unsaturated counterparts. Examples of suitable oxygenate compounds include, but are not limited to: methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Preferred oxygenate compounds are methanol, dimethyl ether, or a mixture thereof. The most preferred oxygenate compound is methanol.

The process for making an olefin product from an oxygenate feedstock by contacting the oxygenate feedstock with a catalyst comprising a silicoaluminophosphate of the present invention has good catalytic performances, which is reflected by a selectivity to ethylene and propylene equal to or greater than 75.0%, and/or an ethylene to propylene ratio equal to or greater than 0.75 and/or a selectivity to propane equal to or lower than 1.0%.

The method of making the olefin products from an oxygenate feedstock can include the additional step of making the oxygenate feedstock from hydrocarbons such as oil, coal, tar sand, shale, biomass and natural gas. Methods for making oxygenate feedstocks are known in the art. These methods include fermentation to alcohol or ether, making synthesis gas, then converting the synthesis gas to alcohol or ether. Synthesis gas can be produced by known processes such as steam reforming, autothermal reforming and partial oxidization.

One skilled in the art will also appreciate that the olefin products made by the oxygenate-to-olefin conversion reaction using the molecular sieve of the present invention can be polymerized to form polyolefins, particularly polyethylenes and polypropylenes. Processes for forming polyolefins from olefins are known in the art. Catalytic processes are preferred. Particularly preferred are metallocene, Ziegler/Natta and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting the olefin product with a polyolefin-forming catalyst at a pressure and temperature effective to form the polyolefin product.

A preferred polyolefin-forming catalyst is a metallocene catalyst as described in U.S. Pat. No. 5,324,800. The preferred temperature range of operation is between 50 and 240° C. and the reaction can be carried out at low, medium or high pressure, being anywhere within the range of about 1 to 200 bars. For processes carried out in solution, an inert diluent can be used, and the preferred operating pressure range is between 10 and 150 bars, with a preferred temperature range of between 120 and 230° C. For gas phase processes, it is preferred that the temperature generally be within a range of 60 to 160° C., and that the operating pressure be between 5 and 50 bars.

In addition to polyolefins, numerous other olefin derivatives may be formed from the olefins recovered from this invention. These include, but are not limited to, aldehydes, alcohols, acetic acid, linear alpha olefins, vinyl acetate, ethylene dichloride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes. The methods of manufacturing these derivatives are well known in the art, and therefore, are not discussed herein.

EXAMPLES

The following examples illustrate specific embodiments within the overall scope of the invention as claimed.

In these examples, the XRD diffraction patterns were recorded on a SCINTAG X2 X-Ray Powder Diffractometer (Scintag Inc. USA), using copper $K\alpha$ radiation. The molecular sieve samples were calcined after preparation and kept moisture-free according to the following procedure:

About 2 grams of molecular sieve were heated-up from room temperature to 200° C. under a flow of nitrogen at a rate of 2° C. per minute. The temperature was held at 200° C. for 30 minutes. Then the sample was heated-up from 200° C. to 650° C. under nitrogen at a rate of 2° C. per minute. The sample was held at 650° C. under nitrogen for 5 hours. Nitrogen was then replaced by air and the sample was kept at 650° C. under air for 3 hours. The sample was then cooled to 200° C. and kept at 200° C. to prevent hydration. The hot sample was then transferred into the XRD sample cup and was covered by Mylar foil to prevent hydration. XRD diffraction patterns were recorded in the $2\theta$ range of 12 to 24 degrees.

DIFFaX analysis was used to determine the AEI/CHA ratio of the molecular sieves. Powder XRD diffraction patterns for varying ratios of AEI/CHA were generated using the DIFFaX program available from the International Zeolite Association (see also M. M. J. Tracey et al., Proceedings of the Royal Chemical Society, London, A (1991), Vol. 433, pp. 499–520 "Collection of Simulated XRD Powder Patterns for Zeolites" by M. M. J. Treacy and J. B. Higgins, 2001, Fourth Edition, published on behalf of the Structure Commission of the International Zeolite Association). Table 2 gives the DIFFaX input file used to simulate the XRD diffraction patterns. For the purposes of this analysis, calculations were based on a random distribution of the layers. Such calcaulations are used for statistical purposes only, and do not mean that the true nature of the material is necessarily random. The simulation diffraction patterns were then compared with the experimental powder XRD diffraction patterns.

TABLE 2

Input file used to simulate XRD diffraction patterns with DIFFaX.

```
{data File for Random AEI-CHA Intergrowths - Starting from an AEI Unit Cell}
{This file is for a 75% probability of a transition generating CHA-type cages}
{             and a 25% probability of a transition generating AEI-type cages)
INSTRUMENTAL                       {Header for instrumental section}
X-RAY                              {Simulate X-ray diffraction}
1.5418                             {X-ray wavelength}
PSEUDO-VOIGT 0.1 -0.036 0.009 0.6  {Instrumental broadening (much slower)}
STRUCTURAL                         {Header for structural section}
13.711 12.731 18.57 90.            {unit cell coordinates a, b, c, and gamma}
UNKNOWN                            {P1 - all coordinates given}
2                                  {Layer 1 and Layer 2}
infinite                           {Layers are very wide in the a-b plane}
LAYER 1
NONE
```

| | | | | | |
|---|---|---|---|---|---|
| Al | 11 | 0.885410 | 0.951850 | 0.168520 | 1.5 1.0 |
| Al | 12 | 0.385410 | 0.451850 | 0.168520 | 1.5 1.0 |
| Al | 13 | 0.114590 | 0.048150 | -.168520 | 1.5 1.0 |
| Al | 14 | 0.614590 | 0.548150 | -.168520 | 1.5 1.0 |
| Al | 21 | 0.881620 | 0.230480 | -.059470 | 1.5 1.0 |
| Al | 22 | 0.381620 | 0.730480 | -.059470 | 1.5 1.0 |
| Al | 23 | 0.118380 | 0.769520 | 0.059470 | 1.5 1.0 |
| Al | 24 | 0.618380 | 0.269520 | 0.059470 | 1.5 1.0 |
| Al | 31 | 0.220800 | 0.094820 | 0.051200 | 1.5 1.0 |
| Al | 32 | 0.720800 | 0.594820 | 0.051200 | 1.5 1.0 |
| Al | 33 | 0.779200 | 0.905180 | -.051200 | 1.5 1.0 |
| Al | 34 | 0.279200 | 0.405180 | -.051200 | 1.5 1.0 |
| P | 41 | 0.779200 | 0.101060 | 0.055650 | 1.5 1.0 |
| P | 42 | 0.279200 | 0.601060 | 0.055650 | 1.5 1.0 |
| P | 43 | 0.220800 | 0.898940 | -.055650 | 1.5 1.0 |

TABLE 2-continued

| | | | | | | |
|---|---|---|---|---|---|---|
| P | 44 | 0.720800 | 0.398940 | −.055650 | 1.5 | 1.0 |
| P | 51 | 0.113750 | 0.236960 | −.062850 | 1.5 | 1.0 |
| P | 52 | 0.613750 | 0.736960 | −.062850 | 1.5 | 1.0 |
| P | 53 | 0.886250 | 0.763040 | 0.062850 | 1.5 | 1.0 |
| P | 54 | 0.386250 | 0.263040 | 0.062850 | 1.5 | 1.0 |
| P | 61 | 0.119660 | 0.962530 | 0.166920 | 1.5 | 1.0 |
| P | 62 | 0.619660 | 0.462530 | 0.166920 | 1.5 | 1.0 |
| P | 63 | 0.880340 | 0.037470 | −.166920 | 1.5 | 1.0 |
| P | 64 | 0.380340 | 0.537470 | −.166920 | 1.5 | 1.0 |
| O | 71 | 0.168130 | 0.057460 | 0.132520 | 3.0 | 1.0 |
| O | 72 | 0.668130 | 0.557460 | 0.132520 | 3.0 | 1.0 |
| O | 73 | 0.831870 | 0.942540 | −.132520 | 3.0 | 1.0 |
| O | 74 | 0.331870 | 0.442540 | −.132520 | 3.0 | 1.0 |
| O | 81 | 0.141650 | 0.178130 | 0.005340 | 3.0 | 1.0 |
| O | 82 | 0.641650 | 0.678130 | 0.005340 | 3.0 | 1.0 |
| O | 83 | 0.858350 | 0.821870 | −.005340 | 3.0 | 1.0 |
| O | 84 | 0.358350 | 0.321870 | −.005340 | 3.0 | 1.0 |
| O | 91 | 0.005220 | 0.261180 | −.061110 | 3.0 | 1.0 |
| O | 92 | 0.505220 | 0.761180 | −.061110 | 3.0 | 1.0 |
| O | 93 | 0.994780 | 0.738820 | 0.061110 | 3.0 | 1.0 |
| O | 94 | 0.494780 | 0.238820 | 0.061110 | 3.0 | 1.0 |
| O | 101 | 0.850040 | 0.181060 | 0.024720 | 3.0 | 1.0 |
| O | 102 | 0.350040 | 0.681060 | 0.024720 | 3.0 | 1.0 |
| O | 103 | 0.149960 | 0.818940 | −.024720 | 3.0 | 1.0 |
| O | 104 | 0.649960 | 0.318940 | −.024720 | 3.0 | 1.0 |
| O | 111 | 0.824370 | 0.050450 | 0.121850 | 3.0 | 1.0 |
| O | 112 | 0.324370 | 0.550450 | 0.121850 | 3.0 | 1.0 |
| O | 113 | 0.175630 | 0.949550 | −.121850 | 3.0 | 1.0 |
| O | 114 | 0.675630 | 0.449550 | −.121850 | 3.0 | 1.0 |
| O | 121 | 0.009850 | 0.978500 | 0.168460 | 3.0 | 1.0 |
| O | 122 | 0.509850 | 0.478500 | 0.168460 | 3.0 | 1.0 |
| O | 123 | 0.990150 | 0.021500 | −.168460 | 3.0 | 1.0 |
| O | 124 | 0.490150 | 0.521500 | −.168460 | 3.0 | 1.0 |
| O | 131 | 0.144120 | 0.863920 | 0.124490 | 3.0 | 1.0 |
| O | 132 | 0.644120 | 0.363920 | 0.124490 | 3.0 | 1.0 |
| O | 133 | 0.855880 | 0.136080 | −.124490 | 3.0 | 1.0 |
| O | 134 | 0.355880 | 0.636080 | −.124490 | 3.0 | 1.0 |
| O | 141 | 0.329790 | 0.160550 | 0.067710 | 3.0 | 1.0 |
| O | 142 | 0.829790 | 0.660550 | 0.067710 | 3.0 | 1.0 |
| O | 143 | 0.670210 | 0.839450 | −.067710 | 3.0 | 1.0 |
| O | 144 | 0.170210 | 0.339450 | −.067710 | 3.0 | 1.0 |
| O | 161 | 0.814580 | 0.343580 | −.077240 | 3.0 | 1.0 |
| O | 162 | 0.314580 | 0.843580 | −.077240 | 3.0 | 1.0 |
| O | 163 | 0.185420 | 0.656420 | 0.077240 | 3.0 | 1.0 |
| O | 164 | 0.685420 | 0.156420 | 0.077240 | 3.0 | 1.0 |
| O | 171 | 0.136560 | 0.169180 | −.128110 | 3.0 | 1.0 |
| O | 172 | 0.636560 | 0.669180 | −.128110 | 3.0 | 1.0 |
| O | 173 | 0.863440 | 0.830820 | 0.128110 | 3.0 | 1.0 |
| O | 174 | 0.363440 | 0.330820 | 0.128110 | 3.0 | 1.0 |
| O | 181 | 0.243600 | 0.983110 | −.000100 | 3.0 | 1.0 |
| O | 182 | 0.743600 | 0.483110 | −.000100 | 3.0 | 1.0 |
| O | 183 | 0.756400 | 0.016890 | 0.000100 | 3.0 | 1.0 |
| O | 184 | 0.256400 | 0.516890 | 0.000100 | 3.0 | 1.0 |
| O | 151 | 0.842490 | 0.949350 | 0.256680 | 3.0 | 1.0 |
| O | 152 | 0.342490 | 0.449350 | 0.256680 | 3.0 | 1.0 |
| O | 155 | 0.157510 | 0.949350 | 0.243320 | 3.0 | 1.0 |
| O | 156 | 0.657510 | 0.449350 | 0.243320 | 3.0 | 1.0 |
| LAYER 2 NONE | | | | | | |
| Al | 15 | 0.114590 | 0.951850 | −.168520 | 1.5 | 1.0 |
| Al | 16 | 0.614590 | 0.451850 | −.168520 | 1.5 | 1.0 |
| Al | 15 | 0.885410 | 0.048150 | 0.168520 | 1.5 | 1.0 |
| Al | 18 | 0.385410 | 0.548150 | 0.168520 | 1.5 | 1.0 |
| Al | 25 | 0.118380 | 0.230480 | 0.059470 | 1.5 | 1.0 |
| Al | 26 | 0.618380 | 0.730480 | 0.059470 | 1.5 | 1.0 |
| Al | 27 | 0.881620 | 0.769520 | −.059470 | 1.5 | 1.0 |
| Al | 28 | 0.381620 | 0.269520 | −.059470 | 1.5 | 1.0 |
| Al | 35 | 0.779200 | 0.094820 | −.051200 | 1.5 | 1.0 |
| Al | 36 | 0.279200 | 0.594820 | −.051200 | 1.5 | 1.0 |
| Al | 37 | 0.220800 | 0.905180 | 0.051200 | 1.5 | 1.0 |
| Al | 38 | 0.720800 | 0.405180 | 0.051200 | 1.5 | 1.0 |
| P | 45 | 0.220800 | 0.101060 | −.055650 | 1.5 | 1.0 |
| P | 46 | 0.720800 | 0.601060 | −.055650 | 1.5 | 1.0 |
| P | 47 | 0.779200 | 0.898940 | 0.055650 | 1.5 | 1.0 |
| P | 48 | 0.279200 | 0.398940 | 0.055650 | 1.5 | 1.0 |
| P | 55 | 0.886250 | 0.236960 | 0.062850 | 1.5 | 1.0 |
| P | 56 | 0.386250 | 0.736960 | 0.062850 | 1.5 | 1.0 |
| P | 57 | 0.113750 | 0.763040 | −.062850 | 1.5 | 1.0 |

TABLE 2-continued

| | | | | | | |
|---|---|---|---|---|---|---|
| P | 58 | 0.613750 | 0.263040 | −.062850 | 1.5 | 1.0 |
| P | 65 | 0.880340 | 0.962530 | −.166920 | 1.5 | 1.0 |
| P | 66 | 0.380340 | 0.462530 | −.166920 | 1.5 | 1.0 |
| P | 67 | 0.119660 | 0.037470 | 0.166920 | 1.5 | 1.0 |
| P | 68 | 0.619660 | 0.537470 | 0.166920 | 1.5 | 1.0 |
| O | 75 | 0.831870 | 0.057460 | −.132520 | 3.0 | 1.0 |
| O | 76 | 0.331870 | 0.557460 | −.132520 | 3.0 | 1.0 |
| O | 77 | 0.168130 | 0.942540 | 0.132520 | 3.0 | 1.0 |
| O | 78 | 0.668130 | 0.442540 | 0.132520 | 3.0 | 1.0 |
| O | 85 | 0.858350 | 0.178130 | −.005340 | 3.0 | 1.0 |
| O | 86 | 0.358350 | 0.678130 | −.005340 | 3.0 | 1.0 |
| O | 87 | 0.141650 | 0.821870 | 0.005340 | 3.0 | 1.0 |
| O | 88 | 0.641650 | 0.321870 | 0.005340 | 3.0 | 1.0 |
| O | 95 | 0.994780 | 0.261180 | 0.061110 | 3.0 | 1.0 |
| O | 96 | 0.494780 | 0.761180 | 0.061110 | 3.0 | 1.0 |
| O | 97 | 0.005220 | 0.738820 | −.061110 | 3.0 | 1.0 |
| O | 98 | 0.505220 | 0.238820 | −.061110 | 3.0 | 1.0 |
| O | 105 | 0.149960 | 0.181060 | −.024720 | 3.0 | 1.0 |
| O | 106 | 0.649960 | 0.681060 | −.024720 | 3.0 | 1.0 |
| O | 107 | 0.850040 | 0.818940 | 0.024720 | 3.0 | 1.0 |
| O | 108 | 0.350040 | 0.318940 | 0.024720 | 3.0 | 1.0 |
| O | 115 | 0.175630 | 0.050450 | −.121850 | 3.0 | 1.0 |
| O | 116 | 0.675630 | 0.550450 | −.121850 | 3.0 | 1.0 |
| O | 117 | 0.824370 | 0.949550 | 0.121850 | 3.0 | 1.0 |
| O | 118 | 0.324370 | 0.449550 | 0.121850 | 3.0 | 1.0 |
| O | 125 | 0.990150 | 0.978500 | −.168460 | 3.0 | 1.0 |
| O | 126 | 0.490150 | 0.478500 | −.168460 | 3.0 | 1.0 |
| O | 127 | 0.009850 | 0.021500 | 0.168460 | 3.0 | 1.0 |
| O | 128 | 0.509850 | 0.521500 | 0.168460 | 3.0 | 1.0 |
| O | 135 | 0.855880 | 0.863920 | −.124490 | 3.0 | 1.0 |
| O | 136 | 0.355880 | 0.363920 | −.124490 | 3.0 | 1.0 |
| O | 137 | 0.144120 | 0.136080 | 0.124490 | 3.0 | 1.0 |
| O | 138 | 0.644120 | 0.636080 | 0.124490 | 3.0 | 1.0 |
| O | 145 | 0.670210 | 0.160550 | −.067710 | 3.0 | 1.0 |
| O | 146 | 0.170210 | 0.660550 | −.067710 | 3.0 | 1.0 |
| O | 147 | 0.329790 | 0.839450 | 0.067710 | 3.0 | 1.0 |
| O | 148 | 0.829790 | 0.339450 | 0.067710 | 3.0 | 1.0 |
| O | 165 | 0.185420 | 0.343580 | 0.077240 | 3.0 | 1.0 |
| O | 166 | 0.685420 | 0.843580 | 0.077240 | 3.0 | 1.0 |
| O | 167 | 0.814580 | 0.656420 | −.077240 | 3.0 | 1.0 |
| O | 168 | 0.314580 | 0.156420 | −.077240 | 3.0 | 1.0 |
| O | 175 | 0.863440 | 0.169180 | 0.128110 | 3.0 | 1.0 |
| O | 176 | 0.363440 | 0.669180 | 0.128110 | 3.0 | 1.0 |
| O | 177 | 0.136560 | 0.830820 | −.128110 | 3.0 | 1.0 |
| O | 178 | 0.636560 | 0.330820 | −.128110 | 3.0 | 1.0 |
| O | 185 | 0.756400 | 0.983110 | 0.000100 | 3.0 | 1.0 |
| O | 186 | 0.256400 | 0.483110 | 0.000100 | 3.0 | 1.0 |
| O | 187 | 0.243600 | 0.016890 | −.000100 | 3.0 | 1.0 |
| O | 188 | 0.743600 | 0.516890 | −.000100 | 3.0 | 1.0 |
| O | 1511 | 0.157510 | 0.050650 | 0.243320 | 3.0 | 1.0 |
| O | 1512 | 0.657510 | 0.550650 | 0.243320 | 3.0 | 1.0 |
| O | 1515 | 0.842490 | 0.050650 | 0.256680 | 3.0 | 1.0 |
| O | 1516 | 0.342490 | 0.550650 | 0.256680 | 3.0 | 1.0 |

```
STACKING                    {Header for stacking description}
recursive                   {Statistical ensemble}
infinite                    {Infinite number of layers}
TRANSITIONS                 {Header for stacking transition data}
{Transitions from layer 1}
0.75   0.0   −0.084    0.5     {layer 1 to layer 1: CHA-type cages}
0.25   0.0    0.0      0.5     {layer 1 to layer 2: AEI-type cages}
{Transitions from layer 2}
0.25   0.0    0.0      0.5     {layer 2 to layer 1: AEI-type cages}
0.75   0.0    0.0857   0.5     {layer 2 to layer 2: CHA-type cages}
```

Example 1

A solution of 33.55 gr of phosphoric acid (85% in water), 32.13 gr of de-mineralized water, and 61.4 gr of a TEAOH solution (35% in water) was prepared in a glass beaker. To this solution were added 3.32 gr of Ludox AS 40 (40% silica). 19.85 gr of alumina (Condea Pural SB) were added and a slurry was obtained with the following composition expressed as molar ratios:

$$0.15 SiO_2/P_2O_5/Al_2O_3/TEAOH/35H_2O$$

This slurry was mixed until homogeneous and transferred to a 150 ml stainless steel autoclave. This autoclave was mounted on a rotating axis in an oven. The axis was rotated at 60 rpm and the oven was heated in 8 hours to 175° C. The autoclave was kept at this temperature for 48 hours. After cooling to room temperature, a sample was taken and washed and dried. An X-ray diffraction pattern was obtained. According to DIFFaX analysis, the AEI/CHA ratio was 15/85 (AEI/CHA=0.18). The silica to alumina molar ratio ($SiO_2/Al_2O_3$) was 0.15. The sample is hereinafter identified as Sample A.

Example 2

67.51 gr of phosphoric acid (85% in water, available from Aldrich) were diluted with 67.29 gr of de-mineralized water.

To this solution were added 123.33 gr of a tetraethylammonium hydroxide solution (35% in water, available from Eastern). Then 2.23 gr of Ludox AS 40 (40% silica from Dupont) were added to this solution. Finally 39.84 gr of alumina (Condea Pural SB) were added and a slurry was obtained. The composition of the mixture can be expressed with the following molar ratios:

0.05SiO$_2$/P$_2$O$_5$/Al$_2$O$_3$/TEAOH/35H$_2$O.

This slurry was mixed until homogeneous and transferred to a 150 ml stainless steel autoclave. This autoclave was mounted on a rotating axis in an oven. The axis was rotated at 60 rpm and the oven was heated in 8 hours to 175 C. The autoclave was kept at this temperature for 48 hours. After cooling to room temperature, a sample was taken and washed and dried and an X-ray diffraction pattern was taken. According to DIFFaX analysis the AEI/CHA ratio was 25/75 (AEI/CHA=0.33). The silica to alumina molar ratio (SiO$_2$/Al$_2$O$_3$) was 0.06. The sample is hereinafter identified as Sample B.

Another sample was prepared using the same procedure, except the autoclave was rotated at 30 rpm instead of 60 rpm. Mixing or tumbling was thus more moderate than in for the preparation of Sample B, which was mixed more vigorously. According to DIFFaX analysis the AEI/CHA ratio was 90/10 (AEI/CHA=0.9). The sample is hereinafter identified as Comparative 1.

Figure 5:
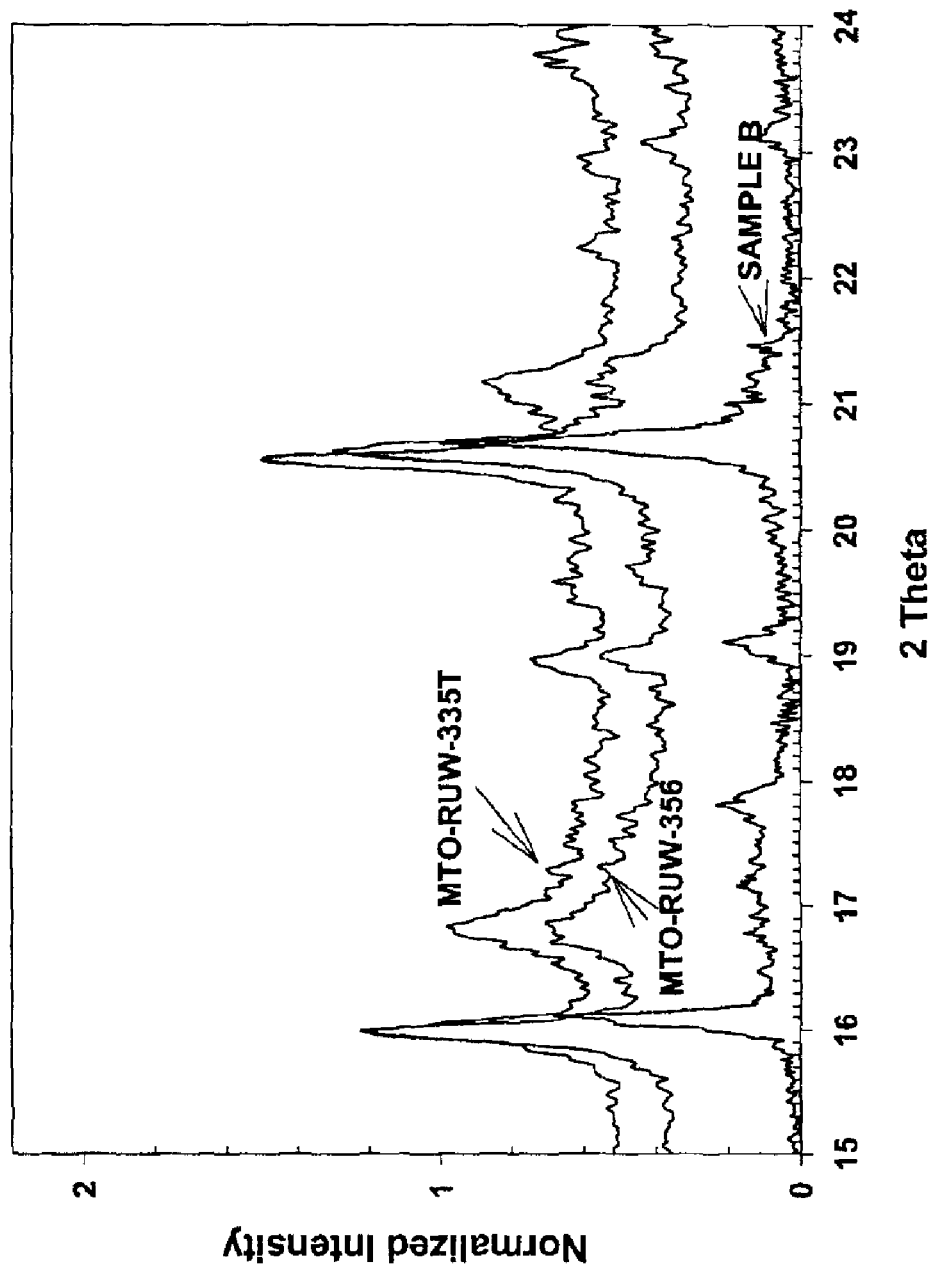
FIG. 5 shows the XRD diffraction pattern of a silicoaluminophosphate molecular sieve according to the invention and, by way of comparison, of MTO-RUW-356 and MTO-RUW-335T of WO 98/15496.

FIGS. 3 and 5 show the X-ray diffraction pattern of Sample B. For comparison purposes, they also show the X-ray diffraction pattern of MTO-RUW-356 described in example 1 and FIG. 1 of WO 98/15496 and of MTO-RUW-335T described in example 3 and FIG. 1 of WO 98/15496. The diffraction patterns of MTO-RUW-356 and MTO-RUW-335T were digitized and re-normalized. DIFFaX analysis of MTO-RUW-356 and MTO-RUW-335T gives AEI/CHA ratios of 2.3 and 4.0, respectively.

Example 3

A solution of 191.23 gr of phosphoric acid (85% in water from Aldrich) and 214.25 gr of de-mineralized water was mixed in a mixing bowl. To this solution 348.71 gr of a tetraethylammonium hydroxide solution (35% in water, Sachem) were added with a burette. After the mixture was homogeneous, 6.04 gr of Ludox AS 40 (40% silica from Dupont) were added. Then 122.33 gr of alumina (Condea Pural SB) were added and the mixture was stirred for 15 minutes. Then 163.46 gr of a tetraethylammonium hydroxide solution (35% in water) were added and 10.13 gr of de-mineralized water. A slurry was obtained with the following composition expressed as molar ratios:

0.045SiO$_2$/0.92P$_2$O$_5$/Al$_2$O$_3$/1.35TEAOH/41H$_2$O

This slurry was mixed until homogeneous and transferred to a 1L PARR autoclave. stainless steel autoclave and the mixture was stirred at 600 rpm during the whole hydrothermal treatment. The autoclave was heated in 5 hours to 175° C. The autoclave was kept at this temperature for 72 hours. After cooling to room temperature, the slurry was washed and dried and a X-ray diffraction pattern was taken. According to DIFFaX analysis the AEI/CHA ratio was 30/70 (AEI/CHA=0.43). The silica to alumina molar ratio (SiO$_2$/Al$_2$O$_3$) was 0.09. The sample is hereinafter identified as Sample C.

Example 4

A solution of 437.92 gr of phosphoric acid (85% in water) and 350.56 gr of de-mineralized water was mixed in a mixing bowl. To this solution 28.49 gr of Ludox AS 40 (40% silica) were added and a hazy solution was obtained. Then 799.09 gr of a tetraethylammonium hydroxide solution (35% in water) were added with a burette and when all TEAOH was added a clear solution was obtained. To this solution 258.29 gr of alumina (Condea Pural SB) were carefully added and also 42.45 gr of de-mineralized water. A slurry was obtained with the following composition expressed as molar ratios:

0.1SiO$_2$/P$_2$O$_5$/Al$_2$O$_3$/TEAOH/34H$_2$O

This slurry was mixed until homogeneous and transferred to a 2L PARR stainless steel autoclave (T316SS) with a jacket welded to the outer wall. The reactor is heated by flowing heated oil from an external heating bath through the double wall. The stainless steel stirrer consists of a combination of a standard PARR anchor stirrer and a standard turbine type impeller. The mixture was stirred at 170 rpm during crystallization. The autoclave was heated in 8 hours to 175° C. The autoclave was kept at this temperature for 36 hours. After cooling to room temperature, the slurry was washed and dried and an X-ray diffraction pattern was taken. According to DIFFaX analysis the AEI/CHA ratio was 30/70 (AEI/CHA=0.43). The silica to alumina molar ratio (SiO$_2$/Al$_2$O$_3$) was 0.14. The sample is hereinafter identified as Sample D.

Example 5

A solution of 434.19 gr of phosphoric acid (85% in water) and 347.58 gr of de-mineralized water was mixed in a mixing bowl. To this solution 28.25 gr of Ludox AS 40 (40% silica) were added and a hazy solution was obtained. Then 792.24 gr of a tetraethylammonium hydroxide solution (35% in water) were added with a burette and when all TEAOH was added a clear solution was obtained. To this solution 256.08 gr of alumina (Condea Pural SB) were carefully added, followed by the addition of a suspension of 0.761 gr of SAPO-34 powder in 10 gr of de-mineralized water (the seed suspension had been put in an ultra-sonic bath for 10 minutes). Also 42.07 gr of de-mineralized water were added to the mixture. A slurry was obtained with the following composition expressed as molar ratios:

0.1SiO$_2$/P$_2$O$_5$/Al$_2$O$_3$/TEAOH/34H$_2$O and 0.04 wt % SAPO-34 seeds

This slurry was mixed until homogeneous and transferred to a 2L stainless steel PARR autoclave and the mixture was stirred at 170 rpm during crystallization. The autoclave was heated in 8 hours to 175° C. The autoclave was kept at this temperature for 36 hours. After cooling the autoclave to room temperature, the crystalline material was removed from the autoclave, washed and dried at 120° C. and an X-ray diffraction pattern was taken. According to DIFFaX analysis, the AEI/CHA ratio was 30/70 (AEI/CHA=0.43). The silica to alumina molar ratio (SiO$_2$/Al$_2$O$_3$) was 0.12. The sample is hereinafter identified as Sample E.

Example 6

A solution of 184.36 gr of phosphoric acid (85% in water) and 176.29 gr of de-mineralized water was mixed in a mixing bowl. To this solution 13.33 gr of Ludox AS 40 (40% silica) were added and a hazy solution was obtained. Then 373.79 gr of a tetraethylammonium hydroxide solution (35% in water) were added with a burette and when all TEAOH was added a clear solution was obtained. To this solution 120.82 gr of alumina (Condea Pural SB) were carefully added and also 31.42 gr of de-mineralized water. A slurry was obtained with the following composition expressed as molar ratios:

$0.1SiO_2/0.9P_2O_5/Al_2O_3/TEAOH/35H_2O$

This slurry was mixed until homogeneous and transferred to a 1L stainless steel PARR autoclave and the mixture was stirred at 170 rpm during crystallization. The autoclave was heated in 8 hours to 175° C. The autoclave was kept at this temperature for 48 hours. After cooling to room temperature, the slurry was washed and dried. X-ray diffraction data was obtained. According to DIFFaX analysis, the AEI/CHA ratio was 20/80 (AEI/CHA=0.25). The silica to alumina molar ratio ($SiO_2/Al_2O_3$) was 0.16. The sample is hereinafter identified as Sample F

Example 7

A solution of 411.23 gr of phosphoric acid (85% in water) and 329.18 gr of de-mineralized water was mixed in a mixing bowl. To this solution 26.75 gr of Ludox AS 40 (40% silica) were added and a hazy solution was obtained. Then 750.35 gr of a tetraethylammonium hydroxide solution (35% in water) were added with a burette and when all TEAOH was added a clear solution was obtained. To this solution 242.59 gr of alumina (Condea Pural SB) were carefully added and also 39.86 gr of de-mineralized water. A slurry was obtained with the following composition expressed as molar ratios:

$0.1SiO_2/P_2O_5/Al_2O_3/TEAOH/34H_2O$

This slurry was mixed until homogeneous and transferred to a 2L stainless steel PARR autoclave and the mixture was stirred at 170 rpm during crystallization. The autoclave was heated in 12 hours to 170° C. The autoclave was kept at this temperature for 24 hours. After cooling to room temperature, a sample was taken, washed and dried and a x-ray diffraction pattern was taken. According to DIFFaX analysis the AEI/CHA ratio was 40/60 (AEI/CHA=0.67). The silica to alumina molar ratio ($SiO_2/Al_2O_3$) was 0.13. The sample is hereinafter identified as Sample G.

Example 8—Comparative 2

This example is presented by way of comparison to illustrate the catalytic performances of an intergrown phase of AEI and CHA molecular sieves where the AEI/CHA ratio is outside the scope of the present invention.

90.74 gr of aluminum isopropoxide were placed in a mixing bowl and 135.29 gr of de-mineralized water were added. This mixture was left static for 10 minutes, after which it was mixed and a gel was obtained. To this gel, 50.19 g of phosphoric acid (85% in water) were added dropwise with a burette, followed by the addition of 3.26 gr of Ludox AS 40 (40% silica). Then 91.54 gr of tetraethylammonium hydroxide solution (35% in water) were added with a burette and also 5.23 gr of de-mineralized water were added. A slurry was obtained with the following composition expressed as molar ratios:

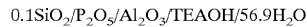

$0.1SiO_2/P_2O_5/Al_2O_3/TEAOH/56.9H_2O$

This slurry was mixed until homogeneous and transferred to a 300 ml steel autoclave. The autoclave was heated in 6 hours to 150° C. The autoclave was kept at this temperature for 133 hours. The crystallization was performed under static conditions. After cooling to room temperature, a sample was taken and washed and dried and an X-ray diffraction pattern was taken. According to DIFFaX analysis, the AEI/CHA ratio was 80/20 (AEI/CHA=4.0). The silica to alumina molar ratio ($SiO_2/Al_2O_3$) was 0.10. The sample is hereinafter identified as Comparative 2.

Example 9

The conversion of methanol to olefins was performed in a tubular, fixed-bed reactor equipped with an on-line gas chromatograph for product analysis. A portion of the tested sample was calcined in nitrogen at 650° C. for 5 hours, followed by heating in air at 650° C. for 3 hours. The calcined molecular sieve was added to the reactor and contacted with a feedstock containing methanol at a temperature of 450° C., a weight hourly space velocity (WHSV) of 25 $hr^{-1}$ and a pressure of 25 psig. The combined ethylene and propylene product selectivity and propane selectivity are shown in Table 3.

In this table, selectivity means the weight average product selectivity of a given product or group of products m with respect to the weight of methanol in the feedstock. It is calculated according to the following mathematical expression:

$$Sm=\Sigma_i(Sm)_i*(MeOH\ conv)_i*(\Delta MeOH/gr\ cat)_i/\Sigma_i(MeOH\ conv)_i*(\Delta MeOH/gr\ cat)_i$$

where $(Sm)_i$ is the midpoint selectivity of m during time on stream interval i;

$(MeOH\ conv)_i$ is the midpoint conversion in time on stream interval i;

$(\Delta MeOH/gr\ cat)_i$= the amount of methanol fed per gram of catalyst during time on stream interval i.

All selectivities were calculated on a coke-free basis.

Table 3 shows that the molecular sieves of the present invention exhibit high selectivities for light olefins and produce few side-products. In Table 3, the selectivities are expressed as percentages.

Having now fully described this invention, it will be appreciated by those skilled in the art that the invention can be performed within a wide range of parameters within what is claimed, without departing from the spirit and scope of the invention.

TABLE 3

Methanol to olefin catalytic performances

| Sample | SiO$_2$/Al$_2$O$_3$ | AEI/CHA* | Ethylene selectivity (%) | Propylene selectivity (%) | Ethylene + propylene selectivity (%) | Propane selectivity (%) | C4 + selectivity** (%) | Ethylene to propylene ratio |
|---|---|---|---|---|---|---|---|---|
| A (ex. 1) | 0.15 | 0.18 | 34.9 | 40.8 | 75.7 | 1.0 | 21.4 | 0.86 |
| B (ex. 2) | 0.06 | 0.33 | 33.6 | 42.6 | 76.3 | 0.4 | 21.8 | 0.79 |
| C (ex. 3) | 0.09 | 0.43 | 33.9 | 42.3 | 76.2 | 0.6 | 21.8 | 0.80 |
| D (ex. 4) | 0.14 | 0.43 | 34.4 | 41.1 | 75.5 | 0.7 | 21.9 | 0.84 |
| E (ex. 5) | 0.12 | 0.43 | 35.1 | 40.8 | 75.9 | 0.9 | 21.4 | 0.86 |
| F (ex. 6) | 0.16 | 0.25 | 35.9 | 40.0 | 75.9 | 1.0 | 21.1 | 0.90 |
| G (ex. 7) | 0.13 | 0.67 | 34.2 | 41.4 | 75.6 | 0.6 | 21.1 | 0.83 |
| Comparative 1 (ex. 2) | | 9.0 | 29.6 | 42.5 | 72.1 | 0.7 | 25.0 | 0.69 |
| Comparative 2 (ex. 8) | 0.10 | 4.0 | 30.0 | 43.3 | 73.3 | 0.9 | 24.3 | 0.69 |

*Determined by DIFFaX
**Selectivity for hydrocarbons having 4 or more carbon atoms

What is claimed is:

1. A silicoaluminophosphate molecular sieve comprising at least one intergrown phase of molecular sieves having AEI and CHA frameworks, wherein said intergrown phase has an AEI/CHA ratio of from about 5/95 to 40/60 as determined by DIFFaX analysis and having no reflection peak in the 9.8 to 12.0 (2θ) range, using the powder X-ray diffraction pattern of a calcined sample of said silicoaluminophosphate molecular sieve.

2. The silicoaluminophosphate molecular sieve of claim 1, wherein said intergrown phase has an AEI/CHA ratio of from about 7/93 to 38/62.

3. The silicoaluminophosphate molecular sieve of claim 1, wherein said intergrown phase has an AEI/CHA ratio of from about 8/92 to 35/65.

4. The silicoaluminophosphate molecular sieve of claim 1, wherein said intergrown phase has an AEI/CHA ratio of from about 9/91 to 33/67.

5. The silicoaluminophosphate molecular sieve of claim 1 wherein the molecular sieve having CHA framework is SAPO-34.

6. The silicoaluminophosphate molecular sieve of claim 1 wherein the molecular sieve having AEI framework is SAPO-18, ALPO-18 or a mixture of SAPO-18 and ALPO-18.

7. The silicoaluminophosphate molecular sieve of claim 1 wherein said silicoaluminophosphate molecular sieve has an X-ray diffraction pattern having at least one reflection peak in each of the following ranges in the 5 to 25 (2θ) range:

| 2θ (CuKα) |
|---|
| 9.3–9.6 |
| 12.7–13.0 |
| 13.8–14.0 |
| 15.9–16.1 |
| 17.7–18.1 |
| 18.9–19.1 |
| 20.5–20.7 |
| 23.7–24.0 |

8. The silicoaluminophosphate molecular sieve of claim 7 wherein the X-ray diffraction pattern has no broad feature centered at about 16.9 (2θ).

9. The silicoaluminophosphate molecular sieve of claim 7 wherein the reflection peak in the 17.7–18.1 (2θ) range has a relative intensity between 0.09 and 0.40 with respect to the reflection peak at 17.9 (2θ) in the diffraction pattern of SAPO-34, all diffraction patterns being normalized to the intensity value of the reflection peak in the 20.5–20.7 (2θ) range.

10. The silicoaluminophosphate molecular sieve of claim 9 wherein the reflection peak in the 17.7–18.1 (2θ) range has a relative intensity between 0.10 and 0.35 with respect to the reflection peak at 17.9 (2θ) in the diffraction pattern of SAPO-34.

11. The silicoaluminophosphate molecular sieve of claim 1 wherein the silica to alumina molar ratio (SiO$_2$/Al$_2$O$_3$) ranges from 0.01 to 0.25.

12. The silicoaluminophosphate molecular sieve of claim 11 wherein the silica to alumina molar ratio (SiO$_2$/Al$_2$O$_3$) ranges from 0.02 to 0.20.

13. The silicoaluminophosphate molecular sieve of claim 11 wherein the silica to alumina molar ratio (SiO$_2$/Al$_2$O$_3$) ranges from 0.03 to 0.19.

14. The silicoaluminophosphate molecular sieve of claim 1, wherein the molecular sieve is comprised of crystalline plates, platelets or stacked platelets.

15. The silicoaluminophosphate molecular sieve of claim 14 wherein the average smallest crystal dimension of the molecular sieve is less than 0.1 micron.

16. A catalyst comprising the silicoaluminophosphate molecular sieve of claim 1 and a binder.

* * * * *